United States Patent [19]

Chae et al.

[11] Patent Number: 6,162,441
[45] Date of Patent: Dec. 19, 2000

[54] METHOD FOR THE PRODUCTION OF ANTI-ESCHERICHIA. COLI O157 : H7 ANTIBODY

[75] Inventors: Hyun-Seok Chae; Dong-Woon Kim; Chong-Nam Ahn, all of Suwon; Sung-Geun Cho, Anyang, all of Rep. of Korea; Jeong-Seok Sim, Edmonton, Canada; Yong-Gon Kim, Suwon, Rep. of Korea

[73] Assignee: Republic of Korea (Management: Rural Development Administration), Suwon, Rep. of Korea

[21] Appl. No.: 09/461,919

[22] Filed: Dec. 15, 1999

[51] Int. Cl.[7] .......................... A61K 39/09; A61K 39/40; B28B 17/00; C07K 16/00
[52] U.S. Cl. ...................... 424/241.1; 424/803; 530/853; 530/389.5
[58] Field of Search ................................ 530/853, 389.5; 424/803, 241.1

[56] References Cited

U.S. PATENT DOCUMENTS 5,585,098  12/1996  Coleman .

OTHER PUBLICATIONS

Patterson et al. J Immunol, 1962, 89:272–278.
Yokoyama et al. Infec & Immun., 1992, 60:998–1007
Fertel et al., BBRC, 102:1028–1033, 1981.
Shimizu et al., J Food Sci., 53:1360–1366, 1988.

*Primary Examiner*—Christina Y. Chan
*Assistant Examiner*—Gerald R. Ewoldt
*Attorney, Agent, or Firm*—Nawrocki, Rooney & Sivertson, P.A.

[57] ABSTRACT

Disclosed is a method for producing anti-*E. coli* O157 antibodies. Anti-*E. coli* O157:H7 antibodies are produced in egg-laying hens and isolated from the eggs. *E. coli* O157:H7 is cultured in a brain heart infusion broth and killed by the treatment with hot water for 5–10 min. After being collected by centrifugation, the dead bacteria is homogenized. Serving as an antigenic material, the bacterial homogenate is injected into egg-laying hens to induce antibodies against *E. coli* O157:H7 in the eggs. The induced antibodies are isolated from the yolk of the eggs and the eggs containing the antibodies against *E. coli* O157:H7 can be utilized, in their entirety, for foods. Alternatively, the yolks are separated from the eggs and freeze-dried. The resulting dried egg component can be applied to processed foodstuffs, alone or in combination with whole eggs. Since the antibodies against *E. coli* O157:H7 are contained in frozen eggs, it is very convenient to store the antibodies. The storage in the frozen eggs also makes it possible to apply the antibodies to almost all foods at any time.

2 Claims, 1 Drawing Sheet

[FIG.1]
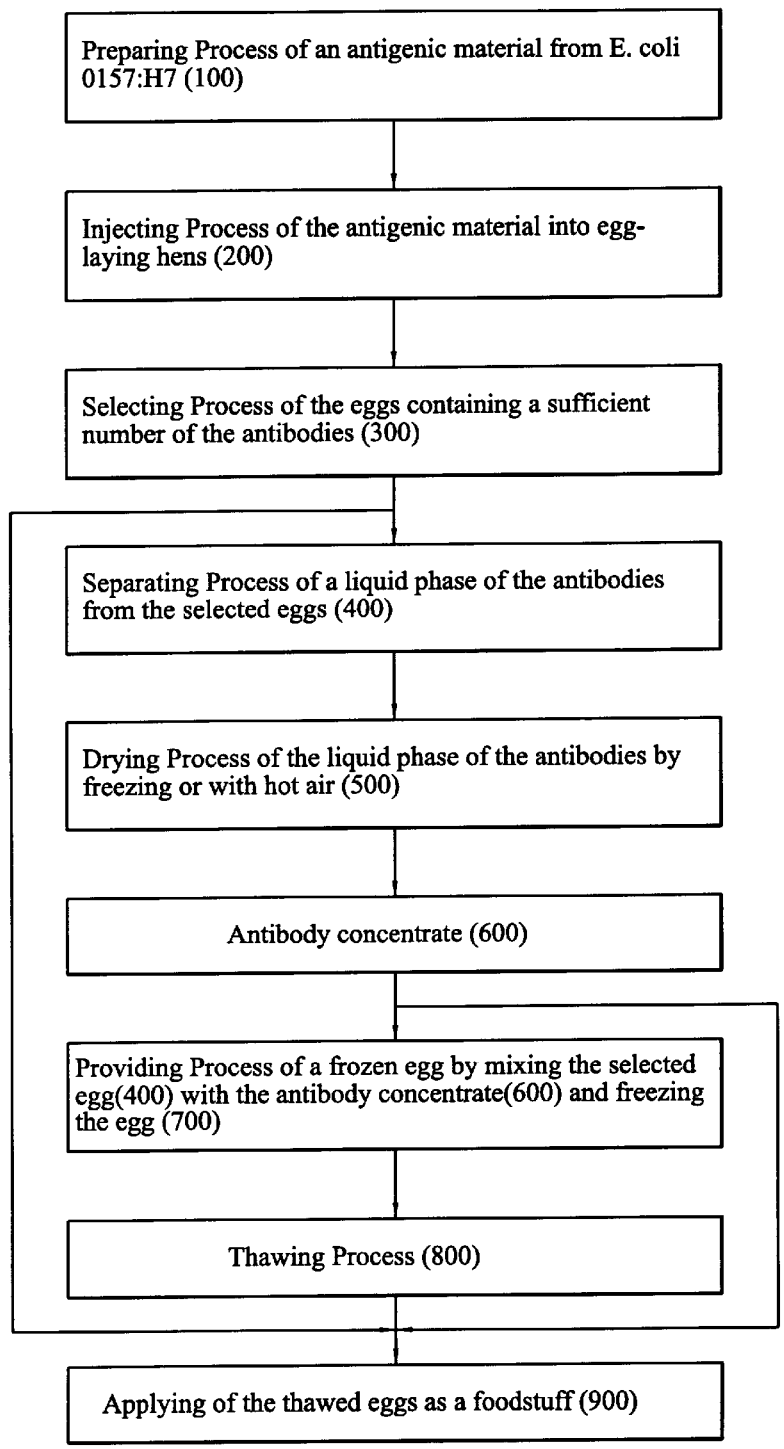

METHOD FOR THE PRODUCTION OF ANTI-*ESCHERICHIA. COLI* O157 : H7 ANTIBODY

BACKGROUND OF THE INVENTION

1. Field of the Invention

The present invention relates, in general, to a method for producing anti-*Escherichia coli* O157:H7 antibodies and, more particularly, to an improvement in the prevention of food toxication caused by *E. coli* O157:H7, along with the method.

2. Description of the Prior Art

First found in U.S.A. in 1982, *Escherichia coli* O157 is a kind of an enteropathogenic *E, coli* which inhabits the intestinal tract of humans or animals causing diarrhea and abdominal pain. On the whole, persons who are infected with *Escherichia coli* O157 usually suffer from hemorrhagic diarrhea. High similarity in shape and size makes it difficult to discriminate the bacteria of interest from typical coliform bacteria via morphological observation. Usually, identification of the bacteria of interest is attained by a serological method in which specific agglutination between antibody and antigen is utilized. In this regard, the taxonomic indicator characteristic of the enteric bacteria of interest is a protein which stands No. 157 in the discovery order of the protein O type antigens which have been found on the surface of *Escherichia coli* bacteria, so it is called O157 or O-157.

*Escherichia coli* O157 is very highly infectious. Generally, this pathogenic bacteria does not cause an attack of a disease without passage of a period of as long as 3.1–8 days after the infection. The long latent period makes it difficult to trace the cause of the infection and to prevent its diffusion. Once infecting human bodies, the pathogenic bacteria produces vero toxin, like dysenteric bacteria, causing abdominal pain and hemorrhagic diarrhea. In addition to breaking red blood cells in the body, the toxic protein attacks the kidney resulting in kidney failure, leading to hemolytic uremia. This disease develops complications in the nervous system, the respiratory system, and the circulatory system and may result in death. Its mortality is found to reach as high as 5–10%. Irrespective of ages, persons, whether they are weak or healthy, can be infected with and seriously afflicted by *Escherichia coli* O157.

In an epidemiological view, *E. coli* O157:H7 usually infiltrates humans through contaminated foods. For example, foods, such as water, ground beef, vegetables, etc, which are contaminated with animal or human excretes, are good intermediate media for the bacteria when not being heated at over about 65° C. Actually, *E. coli*-attributable food poisoning occurred in a mass of elementary school children in 1996, Japan, raising a great social trouble. In America, *E. coli* O157:H7 is widely recognized as a food-poisoning cause to the general public. According to Center for the control of Disease of U.S.A., *E. coli* O157 in ground beef hamburgers is not killed, but causes food toxication when they are cooked at insufficiently high temperatures. Also, it is reported that as many as 20,000 food toxication cases are annually generated, leading 200–500 persons to death.

A reference directed to the detection of *E. coli* O157 is Korean Pat. Laid-Open Publication No. 99-68868, entitled "Monoclonal antibody for detecting Escherichia O157:H7 and its use", in which an immunological diagnosis method using monoclonal antibodies is used to determine rapidly and accurately whether the contamination with *E. coli* O157:H7 occurs. Another detection method for *E. coli* O157 is disclosed in Korean Pat. Laid-Open Publication No. 99-65107, entitled "Method for simultaneously detecting heterogenous genes of *E. coli* O157:H7 using polymerase chain reaction", in which four genes specific for the pathogenic bacteria (two vero toxins, a pathogenic factor attaching to cell walls, and an enzyme-specific gene) are detected by use of PCR. In addition to recognizing the presence of *E. coli* O157:H7 in meat, these methods can be applied for humans and animals. However, these methods are directed to the detection of *E. coli* O157, but not to the production of antibodies against *E. coli* O157.

Conventionally, antibodies have been produced by use of the blood of mammals such as sheep, goats, mice, rabbits, rats, etc. Use of mammalian blood in antibody production, however, always meets with the resistance of environmental organizations or animal rights protection agencies, resulting in low production yield and high cost. As an antigen for eliciting antibodies against *E. coli* O157:H7, the bacteria itself is used after being killed. Alternatively, antigenic materials which are isolated from the bacterial cell membranes are used However, neither of the methods are suitable to be applied for industrialization. For example, the former method is problematic of resulting in a weak binding of antibodies to the antigen. On the other hand, the latter method requires a great deal of time in isolating the antigenic materials, showing economical unfavorableness.

Limited as it is, the production of antibodies in birds has been utilized. From some points of view, antibody production is more advantageous in birds rather than in mammals. For instance, antibodies (IgY) produced in hens are transferred to eggs and then to chickens hatched therefrom as in mammals whose antibodies (IgG) are transferred from mothers to fetuses. The antibody concentration in the yolk of an egg is higher than or as high as in the blood of the hen. Indeed, the antibodies contained in 300 ml of the blood of a hen which lays 20 eggs in a month are as many as those contained in the eggs. More antibodies can be obtained from the eggs by six to seven times than from 40–50 ml of the blood of a rabbit.

SUMMARY OF THE INVENTION

Therefore, it is an object of the present invention to overcome the above problems encountered in prior arts and to provide a method for producing anti-*E. coli* O157:H7 antibodies, in which egg-laying hens are utilized instead of the blood of mammals.

It is another object of the present invention to provide a method for producing anti-*E. coli* O157:H7 antibodies on a large scale and continually.

It is a further object of the present invention to provide a producing method of anti-*E. coli* O157:H7 antibodies, which allows *E. coli* O157:H7-attributable food toxication not to occur.

It is still a further object of the present invention to provide a producing method of anti-*E. coli* O157:H7, which makes it easy to store the antibodies and convenient to use the antibodies.

In the present invention, anti-*E. coli* O157:H7 antibodies are produced in egg-laying hens and isolated from the eggs. To this end, *E. coli* O157:H7, which is identified and isolated from, for example, the excreta of cattle, is cultured in a brain heart infusion broth and killed by the treatment with 90° C. or hotter water for 5–10 min. After being collected by centrifugation, the dead bacteria is crushed with the aid of a sonicator. The crushed bacteria is washed three times with a PBS buffer and freeze-dried to provide an antigen material.

After this antigen material is injected into egg-laying hens, the anti-*E. coli* O157 antibodies produced in the hens are obtained from their eggs. In order to isolate the antibodies from the yolk of the eggs, the yolk is diluted and adjusted to suitable pH values. Conventionally, the pH adjustment is achieved by use of NaOH and/or HCl, which are, however, unsuitable for eating. On the contrary, the present invention uses citric acid and KOH as pH controllers, so that the yolk solution can be applied to foods.

The eggs containing the antibodies against *E. coli* O157:H7 can be utilized, in their entirety, for foods. Alternatively, antibody-concentrated moieties, i.e., yolks, are separated from the eggs and freeze-dried. The resulting dried egg component can be applied to processed foodstuffs, alone or in combination with whole eggs.

BRIEF DESCRIPTION OF THE DRAWING

The above and other objects, features and other advantages of the present invention will be more clearly understood from the following detailed description taken in conjunction with the accompanying drawings, in which:

FIG. 1 is a block diagram showing a process of producing antibodies against *E. coli* O157:H7, according to the present invention.

DETAILED DESCRIPTION OF THE INVENTION

A detail description will be given of the present invention with reference to the accompanying drawing.

FIG. 1 is a process flow of producing anti-*E. coli* O157:H7 antibodies and utilizing them as foodstuffs. As shown in FIG. 1, the process comprises the steps of preparing an antigenic material from *E. coli* O157:H7, injecting the antigenic material into egg-laying hens, selecting the eggs containing a sufficient number of the antibodies, separating a liquid phase of the antibodies from the selected eggs, drying the liquid phase of the antibodies by freezing or with hot air to give an antibody concentrate, mixing the antibody concentrate with ordinary eggs or the antibody-containing eggs and freezing the mixture, thawing the frozen mixture, and applying the thawed eggs as a foodstuff.

In the preparing step, first, *E. coli* O157:H7, *E. coli* is cultured in a brain heart infusion broth and killed by the treatment with 90° C. water for 5–10 min. After being collected by centrifugation (7,000 rpm, 10 min), the bacteria are crushed with the aid of a sonicator. The resulting bacterial fragments are washed three times with a PBS buffer and freeze-dried to give antigenic materials for restraining the proliferation of *E. coli* O157:H7.

In order to produce antibodies against *E. coli* O157:H7, the freeze-dried bacterial fragments are injected into egg-laying hens. In this regard, a solution of the freeze-dried bacterial fragments (1–5 mg) in a PBS buffer (0.5 ml, pH 7.2) is mixed with a Freund's complete adjuvant (0.5 ml) and injected into four sites on the chest of a hen. After two is weeks, a solution of the bacterial fragment (1–5 mg) in a PBS buffer (0.5 ml, pH 7.2) is injected again, along with the Freund's complete adjuvant (0.5 ml) to boost the immunity of the hen.

Of the eggs laid by the injected hens, anti-*E. coli* O157:H7 antibody-containing ones are selected. In order to secure the eggs of highly potent immunity against *E. coli* O157:H7, it is required to determine when the immunity is maintained at the highest level. To this end, the titers which the antibodies show against *E. coli* O157:H7 are measured by ELISA at 405 nm. The ELISA results are given as shown in Table 1, below.

TABLE 1

Change in the Titers of the Antibodies with Time Periods

| Time Period (days) after injection | Unit: ELISA Value, 405 nm | | | | | | | |
|---|---|---|---|---|---|---|---|---|
| | 7 | 14 | 21 | 28 | 35 | 42 | 48 | 56 |
| Ab Titers | 0.03 | 0.12 | 0.23 | 0.32 | 0.35 | 0.41 | 0.56 | 0.55 |

As seen in Table 1, the antibody titers are significantly increased from 0.03 on the $7^{th}$ day after the injection of the antigenic material to 0.41 on the $41^{st}$ day, which indicates that anti-*E. coli* O157:H7 antibodies are formed in the eggs.

From the eggs selected on the basis of the ELISA result, IgY is separated. First, the yolk of an egg is separated from the egg white and diluted with distilled water. Since IgY is readily isolated at about pH 5, the dilution is subjected to pH adjustment. Conventionally, HCl or NaOH has been used for this pH adjustment. In contrast, the present invention employs citric acid or KCH as a pH controller on the account of food application. Citric acid is well known to be helpful in human health.

Following the pH adjustment, the dilution is stored at 4° C. for 6–12 hours and centrifuged at a speed of 7,000 rpm for 20 min. After being filtered, the supernatant is dried at 40–60° C. with the aid of hot air as long as the titers of the antibodies are not decreased. Alternatively, the supernatant is freeze-dried. As a result, an antibody concentrate is obtained. A measurement was made of the titers of the anti-*E. coli* O157:H7 antibodies according to the drying manners. The results are given in the following Table 2.

TABLE 2

Ab Titers of the Antibodies according to the drying manners

| Drying Manners | Freezing Drying | Unit: ELISA value, 405 nm Drying with Hot Air | | |
|---|---|---|---|---|
| | | 40 | 60 | 80 |
| Ab Titer | 0.96 | 0.94 | 0.83 | 0.11 |

The antibody concentrate is mixed with ordinary eggs or with the eggs reinforced with the antibodies against *E. coli* O157:H7. As for the amount of the antibody concentrate, it ranges from 10 to 200 mg (corresponding to an antibody content of 2.8 to 55.6 mg) per ml of the eggs. The resulting egg mixture is subjected to freezing treatment to give frozen eggs. In this connection, salt and sugar are used at an amount of 1–5% and 3–10%, respectively, in order to stabilize the quality of the eggs. These frozen eggs can be used as processed meat foodstuffs, such as hamburger patties, after being thawed.

In order to determine whether the antibody concentrate can restrain the proliferation of *E. coli* O157:H7, a neutralization experiment was conducted in which *E. coli* O157:H7 was grown on media in the presence of various concentrations of the antibody concentrate. In detail, $2 \times 10^2$ cfu/ml of *E. coli* O157:H7 was inoculated on agar plates containing the antibody concentrate at an amount of 5, 10 and 15 mg/mil. After being incubated at 38° C. for 11 hours, the number of the bacteria was counted. The results are given as shown in Table 3, below.

TABLE 3

Neutralization of E. coli O157:H7 with the Ab Concentrates Prepared with Immunized Eggs

| Ab Content (mg/ml) | 0 | 5 | 10 | 15 |
|---|---|---|---|---|
| Nos.of E. coli O157 (cfu/ml) | $6.4 \times 10^7$ | $6.5 \times 10^4$ | $1.5 \times 10^4$ | $9.5 \times 10^4$ | concentration upon inoculation: $2 \times 10^2$ cfu/ml
culturing time period : 11 hours As apparent from the data of Table 3, the antibody concentrate is effective to restrain the proliferation of the pathogenic bacteria. While the bacteria was prosperously grown to the extent of $6.4 \times 10^7$ cfu/ml on the medium treated with no antibody concentrates, they were proliferated only to $1.5 \times 10^4$ cfu/ml on the medium containing the antibody concentrate at an amount of 10 mg/ml.

An observation was made of the effect of the antibody concentrate and the immunized eggs on the proliferation of the bacteria. From an immunized egg, an antibody concentrate was prepared in the same manner as aforementioned. This antibody concentrate was mixed with the yolk of the immunized egg at an amount of 1–2 mg per ml of the yolk and the mixture was stored in a deep freezer. After being thawed, the mixed yolk (4 g) was diluted by ten times with a sterilized physiological saline. E. coli O157:H7 was inoculated at an amount of $2 \times 10^5$ cfu/ml in this medium and cultured at 38° C. for 4 hours. The number of the bacteria was counted. As a control, there was used a medium prepared from the yolk of an ordinary egg which was not immunized with the antigenic material. For comparison, the bacteria was also inoculated on an egg which was previously immunized with the antigenic material, but not frozen, and on an immunized egg which had been frozen and thawed. The results are given in Table 4, below.

TABLE 4

Neutralization of E. coli O157.H7 with Ab-Containing Eggs

| | Control[1] | Whole Egg liquid[2] | Frozen whole Egg liquid[3] | Supplemented with Ab Concentrate[1] |
|---|---|---|---|---|
| Nos. of E.coli | $58.5 \times 10^7$ | $19.6 \times 10^7$ | $18.8 \times 10^7$ | $4.0 \times 10^7$ | note:
[1]ordinary egg not immunized with the antigenic material
[2]containing antibodies
[3]frozen (−20° C.) and thawed
[4]whole egg liquid frozen and thawed
*initial concentration upon inoculation: $2 \times 10^5$ cfu/ml
*culturing time period: 4 hours As seen in Table 4, the bacteria grown in the frozen, whole egg liquid supplemented with the antibody concentrate was fewer by 15 times than those grown in the ordinary egg medium, indicating that the antibodies produced in the immunized egg were effective to restrain the proliferation of the bacteria.

As described hereinbefore, the present invention using birds is simpler in producing anti-E. coli O157:H7 antibodies than conventional methods using the blood of mammals. In addition, more antibodies can be obtained from the immunized eggs by six to seven times than from 40–50 ml of the blood of a rabbit. In practice, one gram of the anti-E. coli O157:H7 antibodies is produced at a cost of U.S. 2,500 dollars when they are prepared from mammals while the production cost can be reduced to only U.S. 10 dollars when advantage is taken of the immunized eggs. Further, these eggs can be used as materials for foods so that restraint can be brought about in the proliferation of E. coli O157:H7, resulting in the protection against food toxication. Moreover, since the antibodies against E. coli O157:H7 are contained in frozen eggs, it is very convenient to store the antibodies. The storage in the frozen eggs also makes it possible to apply the antibodies to almost all foods at any times. Another advantage of the present invention is that the production of the antibodies can be achieved on a large scale without using animal blood as well as is preferable in terms of environmental protection. Furthermore, the present invention will be bring about a significant commercial benefit for livestock raisers because the functional eggs produced according to the present invention can be sold at high costs.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A method for producing anti-E. coli O157:H7 antibodies, comprising the steps of:

preparing an antigenic material from E. coli O157:H7 by culturing E. coli O157:H7 in a brain heart infusion broth, killing the bacteria in the material by treating it with 90–100° C. water for 5–10 min, homogenizing the bacteria with the aid of a sonicator, washing the bacterial homogenate with phosphate buffered saline (PBS), and freeze-drying the homogenate;

inducing anti-E. coli O157:H7 antibodies by initially injecting a mixture comprising a solution of 1–5 mg of the freeze-dried bacterial homogenate in 0.5 ml of PBS buffer, pH 7.2, and 0.5 ml of Freund's complete adjuvant into four sites on the chest of an egg-laying hen and subsequently injecting a solution of the homogenate in 0.5 ml of PBS buffer, pH 7.2, along with 0.5 ml of Freund's complete adjuvant, into the chicken at two weeks after the primary injection, to boost the immunity of the hen; selecting eggs laid by the hen containing a sufficient number of The anti-E. coli O157:H7 antibodies, said eggs being laid at 40–60 days after the primary injection;

separating the yolk of an antibody-containing egg from the white and diluting it with distilled water to form a liquid phase containing the antibodies from the selected eggs;

adjusting the liquid phase to pH 5, storing the liquid phase at 4° C. for 6–12 hours, centrifuging the liquid phase at 7,000 rpm for 20 min, filtering the supernatant, and drying the filtrate by freezing or with hot air to give an antibody concentrate, said antibodies being composed mainly of immunoglobulin Y (IgY).

2. A method as set forth in claim 1, wherein the adjusting of the liquid phase is conducted by use of citric acid or potassium hydroxide.

* * * * *